United States Patent

Urbahns et al.

Patent Number: 5,955,482
Date of Patent: Sep. 21, 1999

[54] USE OF 1,4-DIHYDROPYRIDINE-3,5-DICARBOXYLIC ACID ESTERS AS MEDICAMENTS

[75] Inventors: Klaus Urbahns; Otto Behner; Siegfried Goldmann, all of Wuppertal; Hans-Georg Heine, Krefeld; Bodo Junge, Wuppertal; Rudolf Schohe-Loop, Wuppertal; Egbert Wehinger, Wuppertal; Hartmund Wollweber, Wuppertal; Henning Sommermeyer, Köln; Thomas Glaser, Overath; Reilinde Wittka, Köln; Jean-Marie-Viktor de Vry, Rösrath, all of Germany

[73] Assignee: Bayer Aktiengesellschaft, Leverkusen, Germany

[21] Appl. No.: 08/828,464

[22] Filed: Mar. 28, 1997

Related U.S. Application Data

[62] Division of application No. 08/516,668, Aug. 18, 1995, Pat. No. 5,665,741.

[30] Foreign Application Priority Data

Aug. 25, 1994 [DE] Germany ............ P 44 30 094

[51] Int. Cl.$^6$ ............ A61K 31/44; C07D 211/86
[52] U.S. Cl. ............ 514/356; 546/321
[58] Field of Search ............ 514/356; 546/321

[56] References Cited

U.S. PATENT DOCUMENTS

| | | | |
|---|---|---|---|
| 3,647,807 | 3/1972 | Bossert et al. | 260/295.5 R |
| 3,773,773 | 11/1973 | Bossert | 260/294.8 D |
| 3,883,543 | 5/1975 | Bossert | 260/294.8 D |
| 4,406,906 | 9/1983 | Meyer et al. | 424/263 |
| 5,234,935 | 8/1993 | Behner et al. | 514/356 |
| 5,432,185 | 7/1995 | Behner et al. | 514/356 |

FOREIGN PATENT DOCUMENTS

| | | |
|---|---|---|
| 451654 | 10/1991 | European Pat. Off. |
| 1813436 | 10/1970 | Germany |
| 2815578 | 10/1979 | Germany |

OTHER PUBLICATIONS

P.W.L. Tas, et al., Neuroscience Letters, vol. 94, pp. 279–284, (1988).
X.Y. Wei, et al., Molecular Pharmacology, vol. 35, pp. 541–552, (1989).
J. C. Ellory, et al., Br. J. Pharmacol., vol. 106, pp. 972–977 (1972).
J. C. Ellory, et al. Br. J. Pharmacol., vol. 111, pp. 903–905, (1994).
J. Ellory, et al., FEBS, vol. 296, No. 2, pp. 219–221 (1992).
Chemical Abstracts, vol. 80, No. 17, Abstract No. 95749q, Apr. 29, 1974.

Primary Examiner—Theodore J. Criares
Attorney, Agent, or Firm—Sprung Kramer Schaefer & Briscoe

[57] ABSTRACT

The present invention relates to the use of 1,4-dihydropyridine-3,5-dicarboxylic acid esters, some of which are known, of the general formula (I)

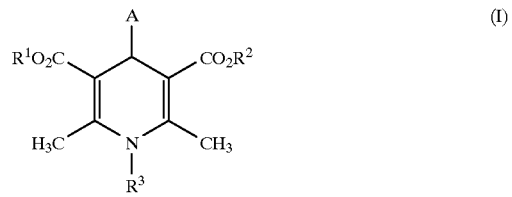

in which

A and $R^1$–$R^3$ have the meaning given in the description, as medicaments, in particular for treatment of the central nervous system, and new selected active compounds.

2 Claims, No Drawings

USE OF 1,4-DIHYDROPYRIDINE-3,5-DICARBOXYLIC ACID ESTERS AS MEDICAMENTS

This application is a divisional of application Ser. No. 08/516,668, filed Aug. 18, 1995, now U.S. Pat. No. 5,665,741.

The present invention relates to the use of 1,4-dihydropyridine-3,5-dicarboxylic acid esters, some of which are known, as medicaments, in particular for treatment of the central nervous system, and to new selected active compounds.

1-Alkyl- and 1-cycloalkyl-(1,4-dihydropyridine)-3,5-dicarboxylic acid esters having a rheological activity are already known from DOS 40 11 695. 1-N-substituted dihydropyridines having a coronary and circulatory action, which influence the vessels of the circulation, are also known from DOS 1 813 436 and DOS 1 923 990. The cerebral action of the specific dihydropyridine nimopidine is already described in DOS 2 815 578.

It has now been found that the 1,4-dihydropyridine-3,5-dicarboxylic acid esters of the general formula (I)

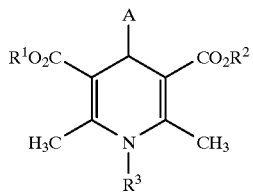

(I)

in which
  A represents aryl having 6 to 10 carbon atoms or pyridyl, which are optionally substituted up to 3-fold in an identical or different manner by nitro, cyano, halogen, trifluoromethyl or by straight-chain or branched alkylthio having up to 6 carbon atoms,
  $R^1$ and $R^2$ are identical or different and represent cycloalkyl having 3 to 6 carbon atoms or represent straight-chain or branched alkyl having up to 8 carbon atoms, which is optionally substituted up to 2-fold in an identical or different manner by straight-chain or branched alkoxy having up to 4 carbon atoms, halogen or by a group of the formula —$NR^4R^5$,
wherein
  $R^4$ and $R^5$ are identical or different and denote hydrogen, benzyl, phenyl or straight-chain or branched alkyl having up to 4 carbon atoms, and
  $R^3$ represents cycloalkyl having 3 to 6 carbon atoms or represents straight-chain or branched alkyl having up to 6 carbon atoms, which is optionally substituted by hydroxyl, phenyl or by straight-chain or branched alkoxy or alkoxycarbonyl having in each case up to 6 carbon atoms,
and salts thereof
surprisingly have a selective modulating action on calcium-dependent potassium channels of high conductivity, and are thus suitable for use in the treatment of the central nervous system, in particular for combating neuronal diseases and for treatment of dementia and depressions and sickle cell anemia.

The present invention preferably relates to the use of those dihydropyridines of the formula (I) which practically have no relevant calcium-agonistic or calcium-antagonistic action in the customary dosage, but have specific modulating actions on potassiun channels.

Compounds which have a selectivity quotient $Q_{sel}$ of at least the value 10 are to be singled out in particular. This selectivity quotient is determined as the quotient of the data of the potassium channel action according to Test 1 and the data from the calcium channel action according to Test 2.

Test 1 (potassium channel action)
$^{86}$Rubidium efflux from C6-BU1 glioma cells The experiments were carried out in accordance with the method described by Tas et al. (Neurosci. Lett. 94, 279–284, (1988)) with slight changes. Rat C6-BU1 glioma cell cultures are used for these. The increase in $^{86}$Rb efflux over the basal efflux caused by ionomycin is calculated from the data and set at 100%. The stimulations in the presence of test substances are then based on this value.

Test 2 (calcium channel action)

The experiments are carried out by the method of D. J. Triggle (Molecular Pharmacol. 35, 541–52 (1989)) with slight deviations. The bonding of substances to the L-Ca channel is determined here by displacement of radioactively labelled $^3$(+)-PN-200-110 on rat cerebral membrane homogenates. The results are expressed as Ki values.

Physiologically acceptable salts are in general salts of the compounds according to the invention with inorganic or organic acids. Preferred salts are those with inorganic acids, such as, for example, hydrochloric acid, hydrobromic acid, phosphoric acid or sulphuric acid, or salts with organic carboxylic or sulphonic acids, such as, for example, acetic acid, maleic acid, fumaric acid, malic acid, citric acid, tartaric acid, lactic acid or benzoic acid, or methanesulphonic acid, ethanesulphonic acid, phenylsulphonic acid, toluenesulphonic acid or naphthalenedisulphonic acid.

The compounds according to the invention can exist in stereoisomeric forms which either behave as mirror images (enantiomers) or do not behave as mirror images (diastereomers). The invention relates both to the antipodes and to the racemic forms as well as the diastereomer mixtures. The racemic forms, like the diastereomers, can be separated into the stereoisomerically uniform constituents in a known manner.

Compounds of the general formula (I) which are preferably used are those
in which
  A represents phenyl, naphthyl or pyridyl, which are optionally substituted up to 3-fold in an identical or different manner by nitro, cyano, fluorine, chlorine, bromine, iodine, trifluoromethyl or by straight-chain or branched alkylthio having up to 4 carbon atoms,
  $R^1$ and $R^2$ are identical or different and represent cyclopropyl, cyclopentyl or cyclohexyl or represent straight-chain or branched alkyl having up to 7 carbon atoms, which is optionally substituted up to 2-fold in an identical or different manner by straight-chain or branched alkoxy having up to 3 carbon atoms, fluorine, chlorine, bromine or by a group of the formula —$NR^4R^5$,
wherein
  $R^4$ and $R^5$ are identical or different and denote hydrogen, benzyl, phenyl or straight-chain or branched alkyl having up to 3 carbon atoms, and
  $R^3$ represents cyclopropyl, cyclopentyl or cyclohexyl or represents straight-chain or branched alkyl having up to 5 carbon atoms, which is optionally substituted by hydroxyl, phenyl or by straight-chain or branched alkoxy or alkoxycarbonyl having in each case up to 5 carbon atoms,
and salts thereof.

Compounds of the general formula (I) which are particularly preferred for combating cerebral diseases are those in which A represents phenyl, naphthyl or pyridyl, which are optionally substituted up to 2-fold in an identical or different manner by nitro, cyano, fluorine, chlorine, bromine, trifluoromethyl or by methylthio, $R^1$ and $R^2$ are identical or different and represent cyclopropyl, cyclopentyl or cyclohexyl or represent straight-chain or branched alkyl having up to 6 carbon atoms, which is optionally substituted up to 2-fold in an identical or different manner by methoxy, fluorine, chlorine, bromine or by a group of the formula —$NR^4R^5$, wherein $R^4$ and $R^5$ are identical or different and denote hydrogen, benzyl, phenyl, methyl or ethyl, and $R^3$ represents cyclopropyl, cyclopentyl or cyclohexyl or represents straight-chain or branched alkyl having up to 5 carbon atoms, which is optionally substituted by hydroxyl, phenyl or by straight-chain or branched alkoxy or alkoxycarbonyl having in each case up to 3 carbon atoms, and salts thereof.

The invention furthermore relates to new selected compounds of the general formula (I) and salts thereof, with the substituent meanings shown in the following table:

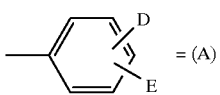
 = (A)

| | $R^2$ | $R^1$ | $R^3$ |
|---|---|---|---|
| 3-$NO_2$, 2-H | —$CH_3$ | —$CH_3$ | —$CH_3$ |
| 3-$NO_2$, 2-H | —$CH_3$ | —$CH_3$ | —$C_2H_5$ |
| 3-$NO_2$, 2-H | —$C_5H_9$ | —$CH_3$ | —$CH_3$ |
| 4-$CF_3$, 2-H | —$CH_3$ | —$CH_3$ | -i-$C_4H_9$ |
| 4-$CF_3$, 2-H | —$CH(CH_2F)_2$ | —$CH_3$ | —$CH_3$ |
| 4-$CF_3$, 2-H | —$CH_3$ | —$CH_3$ | n-$C_4H_9$ |
| 4-$CF_3$, 2-H | —$CH_3$ | —$CH_3$ | —$(CH_2)_3COOCH_3$ |
| 4-$CF_3$, 2-H | —$CH_3$ | —$CH_3$ | —$CH_2OCH_2CH_3$ |
| 4-$CF_3$, 2-H | s-$C_4H_9$ | —$CH_3$ | —$CH_3$ |
| 4-Cl, 2-H | —$CH_3$ | —$CH_3$ | $CH_2C_6H_5$ |
| 4-Cl, 2-H | —$CH_3$ | —$CH_3$ |  |
| 2-Cl, 3-Cl | —$CH_3$ | —$CH_3$ |  |
| 4-F, 3-H | —$CH_3$ | —$CH_3$ | —$CH_2CH(CH_3)_2$ |
| 4-$CF_3$, 3-Cl | —$CH_3$ | —$CH_3$ | —$CH_3$ |
| 4-$CF_3$, 3-Cl | —$CH_3$ | —$CH_3$ |  |
| 4-$CF_3$, 3-Cl | —$CH_3$ | —$CH_3$ | —$CH_2CH_2CH_3$ |
| 3-$CF_3$, 4-Cl | —$CH_3$ | —$CH_3$ | —$CH_2CH_2CH_3$ |
| H, H | —$CH_3$ | —$C_2H_5$ | —$CH_3$ |
| 4-Cl, 3-$CF_3$ | —$CH_3$ | —$CH_3$ |  |
| 4-$CF_3$, 2-H | —$CH_3$ | —$CH_3$ | —$CH_3$ |
| 4-$CF_3$, 2-H | —$CH_3$ | —$CH_3$ | -n-$C_3H_7$ |

The compounds of the general formula (I) can be prepared by customary methods, for example by the processes described in DOS 40 11 695.

The known and new compounds of the general formula (I) according to the invention display an unforeseeable action spectrum.

They are specifically selected channel modulators having a selectivity for calcium-dependent potassium channels of high conductivity (BK(Ca) channels), in particular of the central nervous system.

On the basis of their pharmacological properties, they can be employed for the preparation of medicaments for treatment of centrally degenerative diseases, such as, for example, with the occurrence of dementias (multi-infarction dementia (MD), primary degenerative dementia (PDD), presenile and senile Alzheimer's disease, HIV dementia and other forms of dementia), Parkinson's disease or amyotrophic lateral sclerosis, as well as multiple sclerosis.

The active compounds furthermore are suitable for treatment of age-related disturbances in cerebral performance, organic brain syndrome (OBS) and age-associated memory impairment (AAMI).

They are suitable for the prophylaxis and treatment and for combating the consequences of cerebral circulatory disturbances, such as cerebral ischaemias, apoplexies, craniocerebral traumas and subarachnoid haemorrhages.

They are valuable for the treatment of depressions and psychoses, for example schizophrenia. They are furthermore suitable for treatment of disturbances in neuro-endocrine secretion and in neurotransmitter secretion, and associated disturbances in health, such as mania, alcoholism, drug abuse, addiction or pathological eating behaviour. Other fields of use are the treatment of migraine, sleep disturbances and neuropathies. They are, moreover, suitable as analgesics.

Furthermore, the active compounds are suitable for treatment of disturbances in the immune system, in particular T lymphocyte proliferation.

The present invention also relates to pharmaceutical formulations which, in addition to inert, non-toxic, pharmaceutically suitable auxiliaries and excipients, comprise one or more compounds of the general formula (I), or which consist of one or more active compounds of the formula (I), and to processes for the preparation of these formulations.

The active compounds of the formula (I) should be present in these formulations in a concentration of 0.1 to 99.5% by weight, preferably 0.5 to 95% by weight, of the total mixture.

In addition to the active compounds of the formula (I), the pharmaceutical formulations can also comprise other pharmaceutical active compounds.

The abovementioned pharmaceutical formulations can be prepared in the customary manner by known methods, for example with the auxiliary or excipient substance or substances.

In general, it has proved advantageous to administer the active compound or compounds of the formula (I) in total amounts of about 0.01 to about 100 mg/kg, preferably in total amounts of about 1 mg/kg to 50 mg/kg of body weight every 24 hours, if appropriate in the form of several individual doses, in order to achieve the desired result.

If appropriate, however, it may be advantageous to deviate from the amounts mentioned, and in particular as a function of the nature and body weight of the subject treated, of the behaviour of the individual towards the medicament, of the nature and severity of the disease, of the nature of the formulation and administration, and of the time or interval at which administration takes place.

PREPARATION EXAMPLES

The new compounds of Embodiment Examples 1 to 18 were prepared analogously to the methods from DOS 40 11 695.

TABLE 1

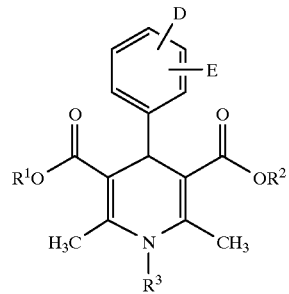

| Example No. | D, E | $R^2$ | $R^1$ | $R^3$ | MS | Melting point (°C.) |
|---|---|---|---|---|---|---|
| 1 | 3-NO$_2$, 2-H | —CH$_3$ | —CH$_3$ | —CH$_3$ | 360 | 132 |
| 2 | 3-NO$_2$, 2-H | —CH$_3$ | —CH$_3$ | —C$_2$H$_5$ | 374 | 103–4 |
| 3 | 3-NO$_2$, 2-H | —C$_5$H$_9$ | —CH$_3$ | —CH$_3$ | 414 | 123 |
| 4 | 4-CF$_3$, 2-H | —CH$_3$ | —CH$_3$ | -i-C$_4$H$_9$ | 425 | 110–5 |
| 5 | 4-CF$_3$, 2-H | —CH(CH$_2$F)$_2$ | —CH$_3$ | —CH$_3$ | 447 | oil |
| 6 | 4-CF$_3$, 2-H | —CH$_3$ | —CH$_3$ | n-C$_4$H$_9$ | 425 | oil |
| 7 | 4-CF$_3$,2-H | —CH$_3$ | —CH$_3$ | —(CH$_2$)$_3$COOCH$_3$ | 469 | 132 |
| 8 | 4-CF$_3$, 2-H | —CH$_3$ | —CH$_3$ | —CH$_2$OCH$_2$CH$_3$ | 427 | 131–3 |
| 9 | 4-CF$_3$, 2-H | s-C$_4$H$_9$ | —CH$_3$ | —CH$_3$ | 425 | oil |
| 10 | 4-Cl, 2-H | —CH$_3$ | —CH$_3$ | —CH$_2$C$_6$H$_5$ | 425 | 170 |
| 11 | 4-Cl, 2-H | —CH$_3$ | —CH$_3$ |  | 375 | 151–4 |

TABLE 1-continued

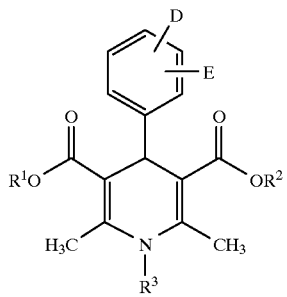

| Example No. | D, E | R² | R¹ | R³ | MS | Melting point (°C.) |
|---|---|---|---|---|---|---|
| 12 | 2-Cl, 3-Cl | —CH₃ | —CH₃ | cyclopropyl | 410 | 182 |
| 13 | 4-F, 3-H | —CH₃ | —CH₃ | —CH₂—CH(CH₃)₂ | 375 | 125 |
| 14 | 4-CF₃, 3-Cl | —CH₃ | —CH₃ | —CH₃ | 417 | 124–6 |
| 15 | 4-CF₃, 3-Cl | —CH₃ | —CH₃ | cyclopropyl | 443 | 115–7 |
| 16 | 4-CF₃, 3-Cl | —CH₃ | —CH₃ | —CH₂CH₂CH₃ | 445 | 92–3 |
| 17 | 3-CF₃, 4-Cl | —CH₃ | —CH₃ | —CH₂CH₂CH₃ | 445 | 79 |
| 18 | H, H | —CH₃ | —C₂H₅ | —CH₃ | 329 | 121–3 |
| 19 | 4-Cl, 3-CF₃ | —CH₃ | —CH₃ | cyclopropyl | | 131–35 |
| 20 | 4-CF₃, 2-H | —CH₃ | —CH₃ | —CH₃ | | 154–55 |
| 21 | 4-CF₃, 2-H | —CH₃ | —CH₃ | n-C₃H₇ | | 102–04 |

We claim:

1. A compound of the formula

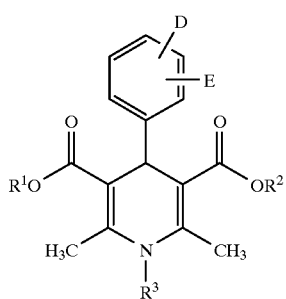

in which

| D,E | R² | R¹ | R³ |
|---|---|---|---|
| 3-NO₂, 2-H | —CH₃ | —CH₃ | —CH₃; |
| 3-NO₂, 2-H | —CH₃ | —CH₃ | —C₂H₅; |
| 3-NO₂, 2-H | —C₅H₉ | —CH₃ | —CH₃; |
| 4-CF₃, 2-H | —CH₃ | —CH₃ | -i-C₄H₉; |

-continued

| D,E | R² | R¹ | R³ |
|---|---|---|---|
| 4-CF₃, 2-H | —CH(CH₂F)₂ | —CH₃ | —CH₃; |
| 4-CF₃, 2-H | —CH₃ | —CH₃ | n-C₄H₉; |
| 4-CF₃, 2-H | —CH₃ | —CH₃ | —(CH₂)₃COOCH₃; |
| 4-CF₃, 2-H | —CH₃ | —CH₃ | —CH₂OCH₂CH₃; |
| 4-CF₃, 2-H | s-C₄H₉ | —CH₃ | —CH₃; |
| 4-Cl, 2-H | —CH₃ | —CH₃ | CH₂C₆H₅; |
| 4-Cl, 2-H | —CH₃ | —CH₃ | cyclopropyl; |
| 2-Cl, 3-Cl | —CH₃ | —CH₃ | cyclopropyl; |
| 4-F, 3-H | —CH₃ | —CH₃ | —CH₂CH(CH₃)₂ |
| 4-CF₃, 3-Cl | —CH₃ | —CH₃ | —CH₃; |

-continued
| D,E | R² | R¹ | R³ |
|---|---|---|---|
| 4-CF₃, 3-Cl | —CH₃ | —CH₃ |  ; |
| 4-CF₃, 3-Cl | —CH₃ | —CH₃ | —CH₂CH₂CH₃; |
| 3-CF₃, 4-Cl | —CH₃ | —CH₃ | —CH₂CH₂CH₃; or |
-continued
| D,E | R² | R¹ | R³ |
|---|---|---|---|
| H, H | —CH₃ | —C₂H₅ | —CH₃ |
or a salt thereof.
2. A pharmaceutical composition which comprises an effective amount of a compound according to claim 1 and an auxiliary or excipient.
* * * * *